(12) United States Patent
Bruneau et al.

(10) Patent No.: US 7,776,075 B2
(45) Date of Patent: Aug. 17, 2010

(54) EXPANDABLE SPINAL RODS AND METHODS OF USE

(75) Inventors: Aurelien Bruneau, Memphis, TN (US); Eric C. Lange, Collierville, TN (US); Randall N. Allard, Germantown, TN (US); Kent M. Anderson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 800 days.

(21) Appl. No.: 11/343,713

(22) Filed: Jan. 31, 2006

(65) Prior Publication Data

US 2007/0191846 A1    Aug. 16, 2007

(51) Int. Cl.
*A61B 17/88* (2006.01)
*A61B 17/70* (2006.01)

(52) U.S. Cl. .................. 606/279; 606/259; 606/262; 606/264; 606/265; 606/266; 606/267; 606/272

(58) Field of Classification Search ......... 606/250–265, 606/278, 279, 86 A, 914, 266, 267, 272
See application file for complete search history.

(56) References Cited

U.S. PATENT DOCUMENTS

| | | | |
|---|---|---|---|
| 5,658,286 A | 8/1997 | Sava | |
| 5,888,220 A | 3/1999 | Felt et al. | |
| 6,106,525 A | 8/2000 | Sachse | |
| 6,336,930 B1* | 1/2002 | Stalcup et al. | 606/284 |
| 6,402,751 B1 | 6/2002 | Hoeck et al. | |
| 6,749,614 B2* | 6/2004 | Teitelbaum et al. | 606/250 |
| 6,821,277 B2* | 11/2004 | Teitelbaum | 606/86 A |
| 6,875,212 B2* | 4/2005 | Shaolian et al. | 606/86 A |
| 6,899,713 B2* | 5/2005 | Shaolian et al. | 606/262 |
| 6,964,667 B2* | 11/2005 | Shaolian et al. | 606/99 |
| 6,986,771 B2* | 1/2006 | Paul et al. | 606/254 |
| 6,989,011 B2* | 1/2006 | Paul et al. | 606/250 |
| 7,008,424 B2* | 3/2006 | Teitelbaum | 606/262 |
| 7,338,527 B2* | 3/2008 | Blatt et al. | 623/17.15 |
| 2002/0095154 A1* | 7/2002 | Atkinson et al. | 606/61 |
| 2002/0161368 A1* | 10/2002 | Foley et al. | 606/61 |
| 2003/0060826 A1* | 3/2003 | Foley et al. | 606/61 |
| 2004/0002708 A1* | 1/2004 | Ritland | 606/61 |
| 2004/0006341 A1 | 1/2004 | Shaolian et al. | |
| 2004/0049190 A1* | 3/2004 | Biedermann et al. | 606/61 |
| 2004/0236327 A1* | 11/2004 | Paul et al. | 606/61 |
| 2004/0236328 A1* | 11/2004 | Paul et al. | 606/61 |
| 2005/0021031 A1* | 1/2005 | Foley et al. | 606/61 |
| 2005/0171543 A1* | 8/2005 | Timm et al. | 606/61 |

(Continued)

FOREIGN PATENT DOCUMENTS

DE    19856013 A1    6/2000

(Continued)

*Primary Examiner*—Eduardo C Robert
*Assistant Examiner*—Ellen C Hammond

(57) ABSTRACT

A spinal rod having first and second end members. The end members may be flexible or rigid. An expandable intermediate section is positioned between the first and second end members. The intermediate section may be axially expandable upon the introduction of a substance into a port that may be located in either of the first and second end members or the intermediate section. The intermediate section may be expandable between a first size, where the first and second end members are spaced a first distance apart, and a second enlarged size, where the first and second end members are spaced a second greater distance apart.

9 Claims, 9 Drawing Sheets

U.S. PATENT DOCUMENTS

| | | | |
|---|---|---|---|
| 2005/0177164 A1* | 8/2005 | Walters et al. | 606/72 |
| 2005/0203519 A1* | 9/2005 | Harms et al. | 606/61 |
| 2005/0209694 A1* | 9/2005 | Loeb | 623/17.11 |
| 2005/0234449 A1* | 10/2005 | Aferzon | 606/61 |
| 2005/0256578 A1* | 11/2005 | Blatt et al. | 623/17.15 |
| 2005/0277922 A1* | 12/2005 | Trieu et al. | 606/61 |
| 2005/0277934 A1* | 12/2005 | Vardiman | 606/61 |
| 2005/0288670 A1* | 12/2005 | Panjabi et al. | 606/61 |
| 2006/0009767 A1* | 1/2006 | Kiester | 606/61 |
| 2006/0009768 A1* | 1/2006 | Ritland | 606/61 |
| 2006/0036240 A1* | 2/2006 | Colleran et al. | 606/61 |
| 2006/0041259 A1* | 2/2006 | Paul et al. | 606/61 |
| 2006/0085073 A1* | 4/2006 | Raiszadeh | 623/17.12 |
| 2006/0085074 A1* | 4/2006 | Raiszadeh | 623/17.12 |
| 2006/0089646 A1* | 4/2006 | Bonutti | 606/61 |
| 2006/0111713 A1* | 5/2006 | Jackson | 606/61 |
| 2006/0111714 A1* | 5/2006 | Foley | 606/61 |
| 2006/0271048 A1* | 11/2006 | Thramann | 606/61 |
| 2007/0016193 A1* | 1/2007 | Ritland | 606/61 |
| 2007/0043360 A1* | 2/2007 | Thramann | 606/61 |

FOREIGN PATENT DOCUMENTS

| | | |
|---|---|---|
| EP | 1574173 A1 | 9/2005 |
| WO | 2004105577 A2 | 12/2004 |

* cited by examiner

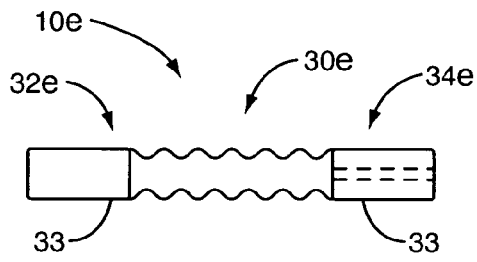
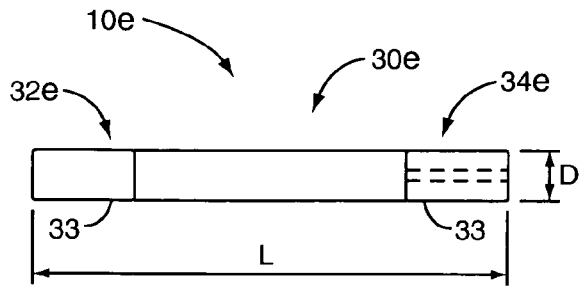
FIG. 7A    FIG. 7B
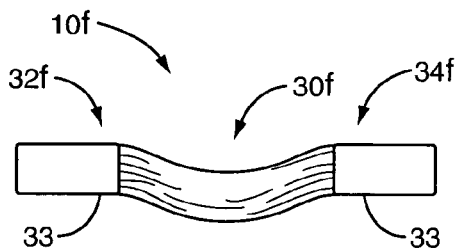
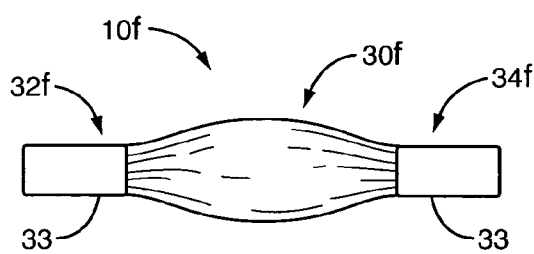
FIG. 8A    FIG. 8B
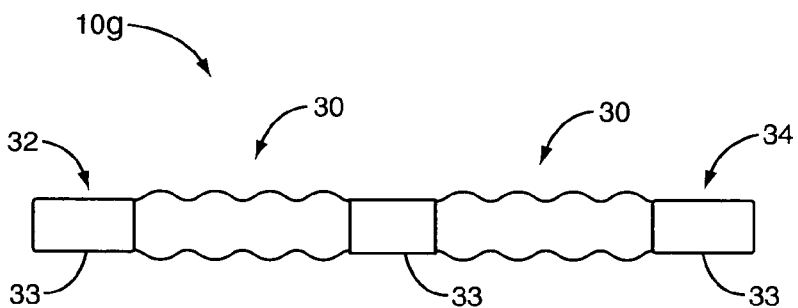
FIG. 9
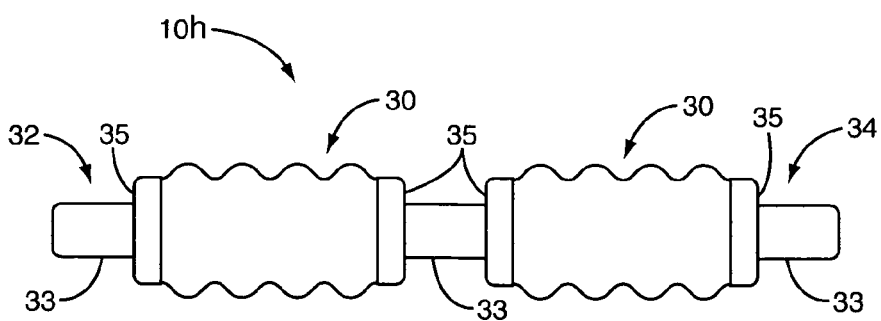
FIG. 10

EXPANDABLE SPINAL RODS AND METHODS OF USE

BACKGROUND

Spinal rods are often used in the surgical treatment of spinal disorders such as degenerative disc disease, disc herniations, scoliosis or other curvature abnormalities, and fractures. Different types of surgical treatments are used. In some cases, spinal fusion is indicated to inhibit relative motion between vertebral bodies. In other cases, dynamic implants are used to preserve motion between vertebral bodies. For either type of surgical treatment, spinal rods may be attached to the exterior of two or more vertebrae, whether it is at a posterior, anterior, or lateral side of the vertebrae. In other embodiments, spinal rods are attached to the vertebrae without the use of dynamic implants or spinal fusion.

Spinal rods may provide a stable, rigid column that encourages bones to fuse after spinal-fusion surgery. Further, the rods may redirect stresses over a wider area away from a damaged or defective region. Also, a rigid rod may restore the spine to its proper alignment. In some cases, a flexible rod may be appropriate. Flexible rods may provide some advantages over rigid rods, such as increasing loading on interbody constructs, decreasing stress transfer to adjacent vertebral elements while bone-graft healing takes place, and generally balancing strength with flexibility. One disadvantage with conventional rods is that their length, which may span several vertebrae, may require large surgical incisions to implant the rod. Therefore, surgical procedures requiring the installation of an elongated rod have often required invasive open procedures that are more costly to perform, and potentially more dangerous and more painful for the patient.

SUMMARY

Illustrative embodiments disclosed herein are directed to a spinal rod that has first and second end members. The first and second end members may comprise a clamping portion for coupling with a vertebral member. In different embodiments, the end members may be flexible or rigid. An expandable intermediate section is positioned between the first and second end members. The intermediate section may be axially expandable upon the introduction of a substance into a port that may be located in either of the first and second end members or the intermediate section. Further, the port may be axially or radially located on the rod. The substance may be a fluid, such as a curable liquid. The intermediate section may be expandable between a first size, where the first and second end members are spaced a first distance apart, and a second enlarged size, where the first and second end members are spaced a second greater distance apart. The intermediate section may be flexible or rigid. The rod may be configured to span two or more vertebrae.

BRIEF DESCRIPTION OF THE DRAWINGS

FIGS. 7A and 7B are lateral views of a spinal rod in compressed and extended states according to one embodiment;

FIGS. 8A and 8B are lateral views of a spinal rod in compressed and extended states according to one embodiment;

FIG. 9 is a lateral view of a spinal rod according to one embodiment;

FIG. 10 is a lateral view of a spinal rod according to one embodiment;

DETAILED DESCRIPTION

Figure 1:
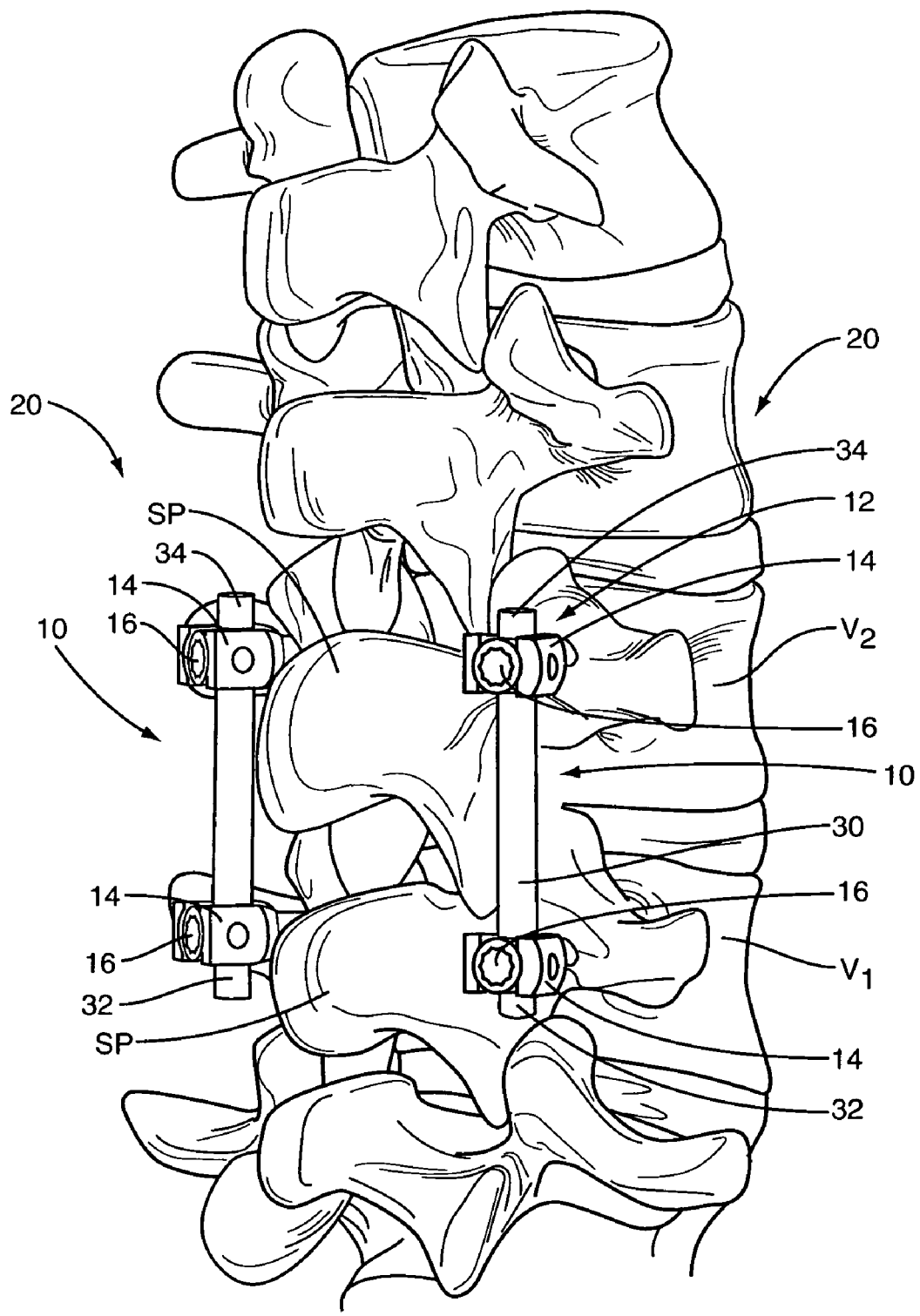
FIG. 1 is a perspective view of first and second assemblies comprising spinal rods attached to vertebral members according to one embodiment.

The various embodiments disclosed herein are directed to spinal rods that are characterized by at least one expandable portion. The expandable portion may be compressed or left unfilled during installation of the rod and may be filled with an injectable substance once the rod is positioned within the body. Various embodiments of a spinal rod may be implemented in a spinal rod assembly of the type indicated generally by the numeral 20 in FIG. 1. FIG. 1 shows a perspective view of first and second spinal rod assemblies 20 in which spinal rods 10 are attached to vertebral members V1 and V2. In the example assembly 20 shown, the rods 10 are positioned at a posterior side of the spine, on opposite sides of the spinous processes SP. Spinal rods 10 may be attached to a spine at other locations, including lateral and anterior locations. Spinal rods 10 may also be attached at various sections of the spine, including the base of the skull and to vertebrae in the cervical, thoracic, lumbar, and sacral regions. In one embodiment, a single rod 10 is attached to the spine. Thus, the illustration in FIG. 1 is provided merely as a representative example of one application of a spinal rod 10.

In one embodiment as illustrated in FIG. 1, the spinal rods 10 are secured to vertebral members V1, V2 by pedicle assemblies 12 comprising a pedicle screw 14 and a retaining cap 16. The outer surface of spinal rod 10 is grasped, clamped, or otherwise secured between the pedicle screw 14 and retaining cap 16. Other mechanisms for securing spinal rods 10 to vertebral members V1, V2 include hooks, cables, and other such devices. Examples of other types of retaining hardware include threaded caps, screws, and pins. Spinal rods 10 are also attached to plates in other configurations. Thus, the exemplary assemblies 12 shown in FIG. 1 are merely representative of one type of attachment mechanism.

Figure 2:
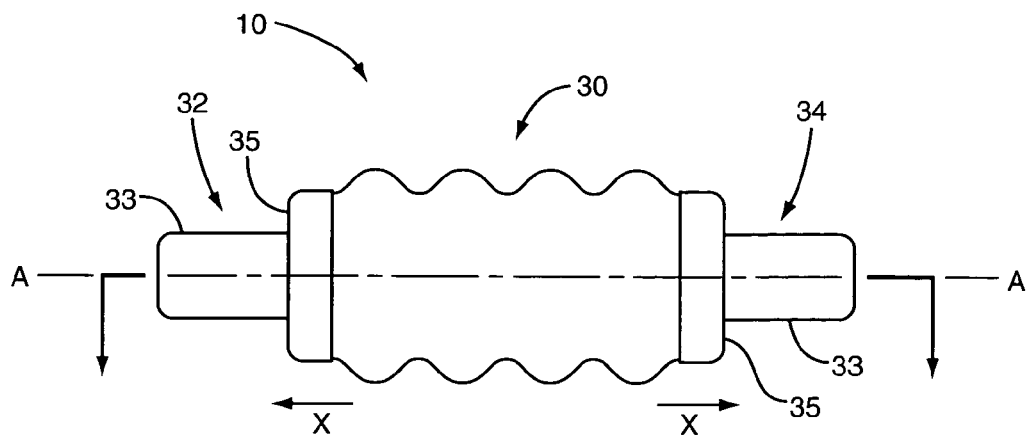
FIG. 2 is a lateral view of a spinal rod according to one embodiment.

FIG. 2 shows an isolated view of a spinal rod 10 of the type used in the exemplary assembly 20 in FIG. 1. The exemplary rod 10 includes an expandable portion 30. A first rod end 32 is shown attached to the left side of the expandable portion 30 in the view provided. A second rod end 34 is also shown attached to the right side of the expandable portion 30. The first and second rod ends 32, 34 further include a clamping portion 33 and an enlarged flange portion 35. The clamping portion 33 may be sized to fit within conventional rod securing devices such as those shown in FIG. 1 and described above. For example, the clamping portion 33 may have a diameter within a range between about 4 and 7 mm. The rod ends 32, 34 may be constructed from a variety of surgical grade materials. These include metals such as stainless steels, cobalt-chrome, titanium, and shape memory alloys. Nonmetallic rods, including polymer rods made from materials such as PEEK and UHMWPE, are also contemplated. The spinal rod 10 may have rigid or flexible rod ends 32, 34.

The expandable portion 30 is axially expandable along the longitudinal axis A of the rod 10 as indicated by the arrows labeled X. In one or more embodiments, the rod 10 may be expanded through the introduction of an injectable substance that contacts the first and second rod ends 32, 34, thereby causing the first and second rod ends 32, 34 to move opposite one another. Various techniques may be used to introduce the injectable substance into the expandable portion 30. For example, one embodiment of a rod 10a depicted in FIG. 3 includes a cannulated second rod end 34a. The duct 36 within the second rod end 34a connects an interior volume 38 with the exterior of the rod 10a. The interior volume 38 is defined by the first and second rod ends 32a, 34a and an expandable outer sheath 42. In the embodiment shown, the sheath 42 connects the first and second rod ends 32a, 34a. In one embodiment, the sheath 42 is constructed of a flexible biomedical grade material including resins, polymers, and metals. An injectable substance may flow through the duct 36 into the interior volume 38 of the expandable portion 30 from an end 40 of the second rod end 34a. As the injectable substance fills the interior volume 38, the substance contacts surfaces 45 and 49, thus forcing the second rod end 34a to separate from the first rod end 32a as indicated by the arrow labeled X. In one embodiment, the rod 10a comprises a self-sealing valve 42 that prevents the injectable substance from escaping once the interior volume 38 is filled. In one embodiment, the self-sealing valve 42 is a check valve that is incorporated along the duct 36 to allow the injectable substance to flow towards the interior volume 38, but not out of the duct 36.

A variety of injectable substances may be inserted into the interior volume to cause the expandable portion 30 to expand. In one embodiment, the injectable substance is a fluid, such as a gas or a liquid. In one embodiment, the injectable substance is a solid, such as a powder. In one embodiment, the injectable substance is a curable liquid that solidifies after a predetermined amount of time or under the influence of an external catalyst. For instance, an injectable liquid may cure under the influence of heat or light, including ultraviolet light. Some examples of in situ curable liquids include epoxy, PMMA, polyurethane, and silicone.

Figure 3:
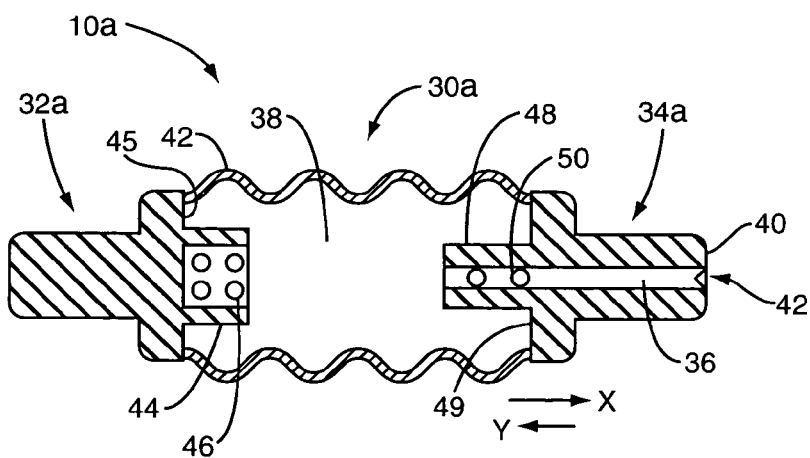
FIG. 3 is a cross section view of a spinal rod according to one embodiment.

The exemplary rod 10a shown in FIG. 3 includes a first perforated protrusion 44 coupled to the first rod end 32a and extending inward from a surface 45. Similarly, the rod 10a includes a second perforated protrusion 48 coupled to the second rod end 34a and extending inward from a surface 49. The first perforated protrusion 44 includes a plurality of holes 46 that allow the injectable substance to flow into or out of the first perforated protrusion 44. Similarly, the second perforated protrusion 48 includes a plurality of holes 50 that allow the injectable substance to flow into or out of the second perforated protrusion 48. In embodiments where the injectable substance comprises a curable liquid, the first and second perforated protrusions 44, 48 may provide an increased amount of surface area for a curable liquid to adhere. This may provide a more secure bond between the curable liquid and the first and second rod ends 32a, 34a.

In one embodiment, the first and second perforated protrusions 44, 48 are cylindrical. In one embodiment, the first perforated protrusion 44 is larger than the second perforated protrusion 48. Thus, in the event the first and second rod ends 32a, 34a are pushed together as indicated by the arrow labeled Y, the second perforated protrusion 48 may fit substantially within the first perforated protrusion 44. In this scenario, the first perforated protrusion 44 may contact the second rod end 34a. Alternatively, the second perforated protrusion 48 may contact the first rod end 32a. In either case, overcompression of the sheath 42 and damage thereto may be avoided.

Figure 4:
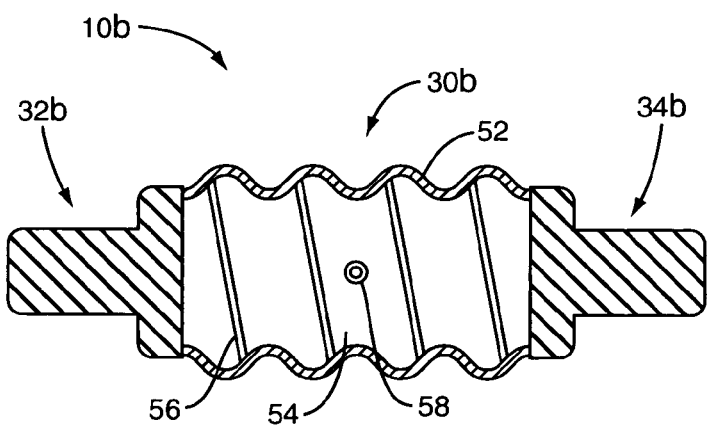
FIG. 4 is a cross section view of a spinal rod according to one embodiment.

An alternative embodiment of a rod 10b is depicted in FIG. 4. In this embodiment, the first and second rod ends 32b, 34b are shown as solid members, though this is not expressly required. The exemplary sheath 52 surrounding the interior volume 54 is an accordion-style bellows. In one embodiment, the sheath 52 is reinforced with a woven or braided structure. In one embodiment, the sheath 52 is reinforced with coiled or concentric wires 56. The concentric wires 56 may be comprised of a biocompatible metal such as stainless steel, titanium alloys, or nitinol. The interior volume 54 of the expandable portion 30b may be filled through a self-sealing valve 58 that prevents an injectable substance from escaping once the interior volume 38 is filled.

Figure 5:
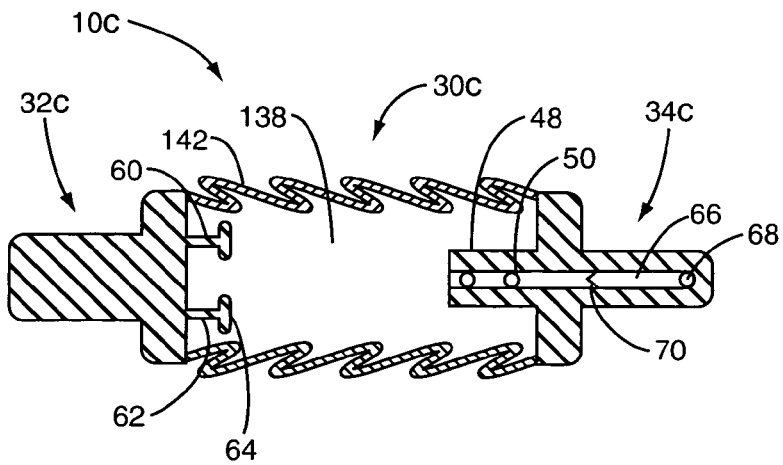
FIG. 5 is a cross section view of a spinal rod according to one embodiment.

FIG. 5 shows an alternative embodiment of a rod 10c that is similar to rod 10a. For instance, the second perforated protrusion 48 and the holes contained thereon 50 are substantially the same on both embodiments of the rod 10a, 10c. In rod 10c, the expandable portion 30c is defined in part by a folded sheath 142 having pleats that overlap one another. When the expandable portion 30c expands under the influence of an injected substance, the folded sheath 142 unfolds to an extended state, such as that shown in FIG. 1.

The first rod end 32c has a plurality of anchors 60 comprising a stem portion 62 and an enlarged head portion 64. In embodiments where the injectable substance comprises a curable liquid, the cured material may harden in the undercuts adjacent the stem portion 62, between the head portion 64 and the first rod end 32c. The anchors 60 may provide a more secure bond between the curable liquid and the first rod end 32c.

The exemplary rod 10c also has a cannulated second rod end 34c with a duct 66 connecting the interior volume 138 with an injection port 68. In the embodiment shown, the injection port 68 is located at a side of the rod end 34c. In one embodiment, the injection port 68 is radially disposed. This is in contrast to the axially disposed port and valve 42 shown in FIG. 3. Injectable materials may be introduced into the duct 66 through the port 68 and ultimately flow into interior volume to expand the expandable portion 30c. In one embodiment, the rod 10c comprises a self-sealing valve 70 that prevents the injectable substance from escaping once the interior volume 38 is filled. In one embodiment, the self-sealing valve 70 is a check valve that is incorporated along the duct 66 to allow the injectable substance to flow towards the interior volume 38, but not out of the duct 66. In an alternative embodiment, the self-sealing valve 70 may be disposed at the injection port 68.

Figure 6A:
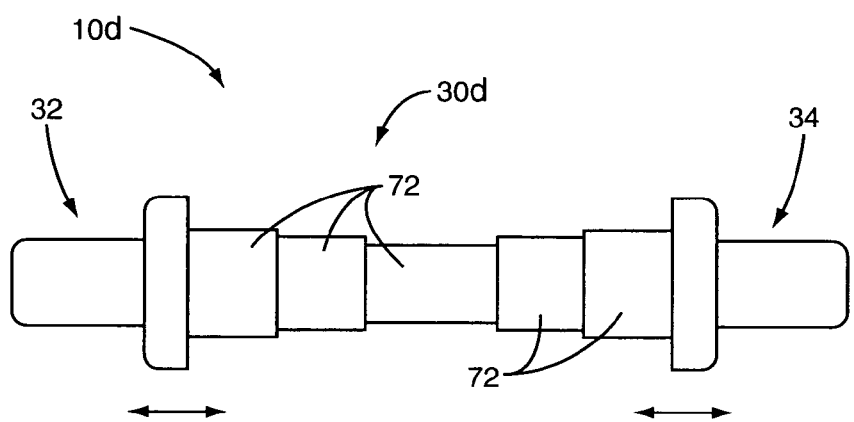
FIGS. 6A and 6B are lateral views of a spinal rod in extended and compressed states according to one embodiment.
Figure 6B:
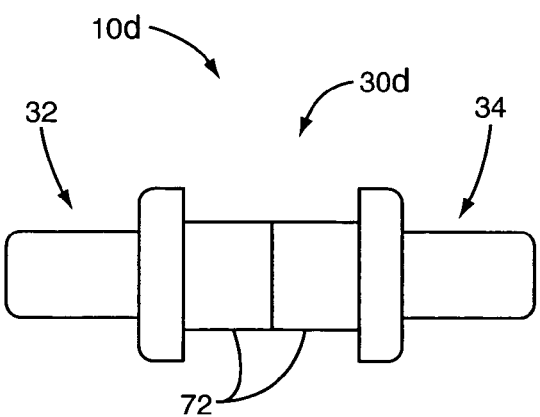

FIGS. 6A and 6B illustrate an alternative embodiment of a rod 10d that is characterized by a telescoping expandable portion 30d. In contrast with previous embodiments that use a flexible sheath or bellows design, the illustrated rod 10d has a series of concentric columns 72 that are able to collapse within one another in the absence of an injectable material within the expandable portion 30d. FIG. 6B illustrates the collapsed rod 10d. However, upon filling the expandable portion 30d with the injectable material, the concentric columns 72 expand or telescope to the expanded position illustrated in FIG. 6A. In one embodiment, the concentric columns 72 are substantially cylindrical. In one embodiment, the concentric columns 72 have a substantially non-circular cross section, including for example, square, oval, star, or polygonal shapes. In one embodiment, the end portions 32, 34 may themselves form concentric columns 72 with the expandable portion 30d being a cavity formed in one or both of the end portions 32,

34. The concentric columns 72 may have seals (not shown) to prevent the injectable substance from escaping once the expandable portion 30d is filled.

FIGS. 7A and 7B illustrate an exemplary rod 10e having different rod ends 32e, 34e than those provided on embodiments described above. In this particular embodiment, the rod ends 32e and 34e do not have an enlarged flange. Instead, the expanding portion 30e is coupled directly to clamping portions 33. Consequently, when the expandable portion 30e is filled with an injectable substance as shown in FIG. 7B, the rod 10e has an outer width D that is substantially uniform over the entire length of the rod 10e. Also, the rod 10e (or other rods 10 described herein) may have an extended length L that is sufficient to span at least one vertebral pair. Thus, the length L may be in the range between about 30-40 mm or greater as needed. Rod 10e may also have a cannulated second rod end 34e. Other means of introducing an injectable substance may be incorporated into rod 10e. This includes variations described above such as the radial insertion points in the rod end 32e, 34e or in the expandable portion 30e.

FIGS. 8A and 8B illustrate an alternative configuration where rod 10f includes an expandable portion 30f constructed of a non-compliant, flexible material 74. That is, the flexible material 74 is balloon-like in that it does not assume any particular shape when unfilled as shown in FIG. 8A. Further, the flexible material 74 of the expandable portion 30f is capable of expanding to a width that is larger than the width of the rod ends 32f, 34f as shown in FIG. 8B.

In embodiments discussed above, the exemplary rods 10 have generally comprised an expandable portion 30 disposed between two rod ends 32, 34. In other embodiments, such as those illustrated in FIGS. 9 and 10, the rods 10g, 10h are comprised of a plurality of expandable portions 30 disposed in an alternating manner between clamping portions 33. With this multi-level configuration, the rods 10g, 10h may be attached to several vertebrae. In the embodiments shown, two expandable portions 30 are arranged in an alternating manner between three clamping portions 33. Accordingly, these embodiments may be attached at three points, possibly at three different vertebrae. Rods 10 comprising a larger number of expandable portions 30 and clamping portions 33 are certainly feasible.

The embodiments illustrated in FIGS. 9 and 10 include multiple expandable portions 30 with each portion 30 having substantially the same size and construction. In some embodiments, the portions 30 have different sizes. In some embodiments, each of the portions 30 is a different type.

Figure 11:
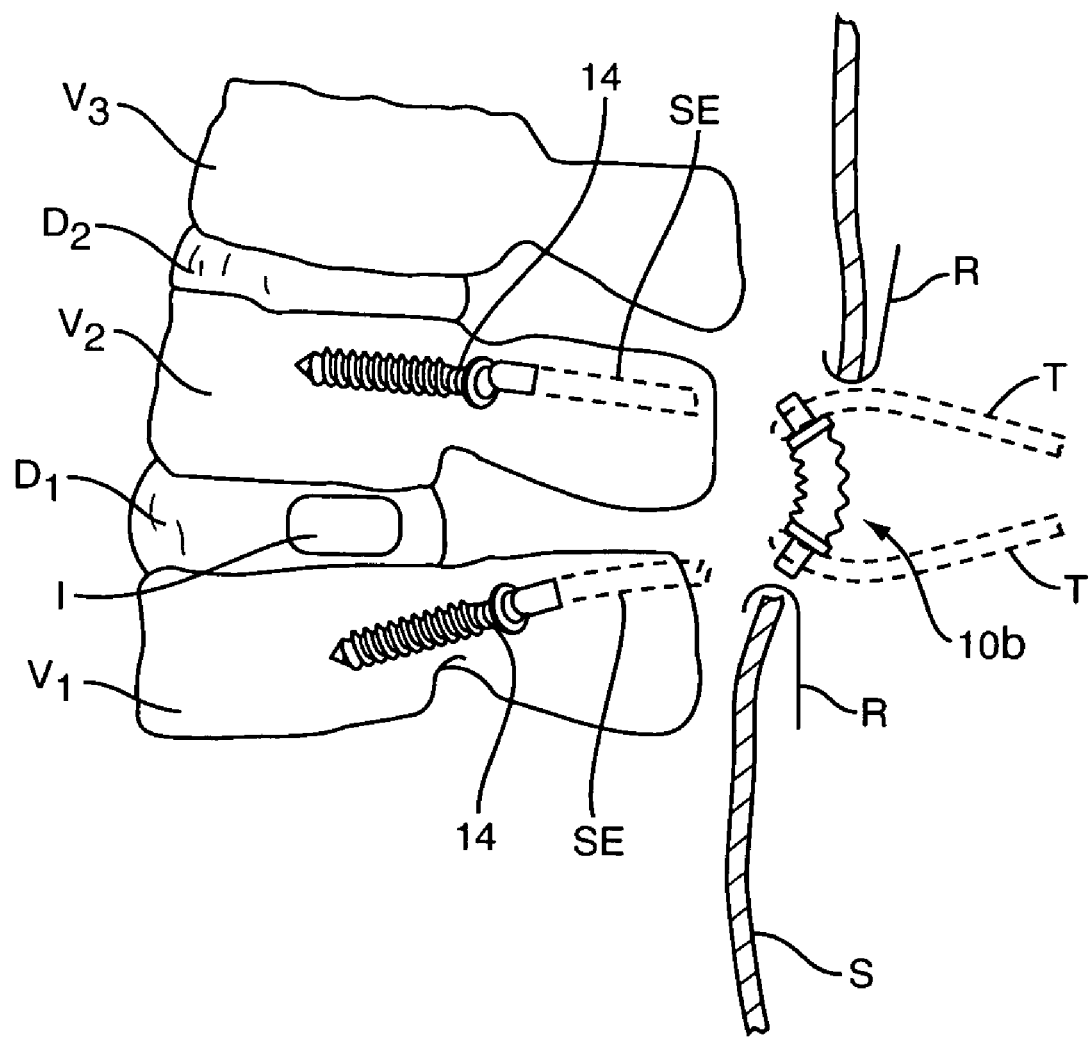
FIGS. 11-13 illustrate a surgical implantation process for a rod according to one embodiment.
Figure 12:
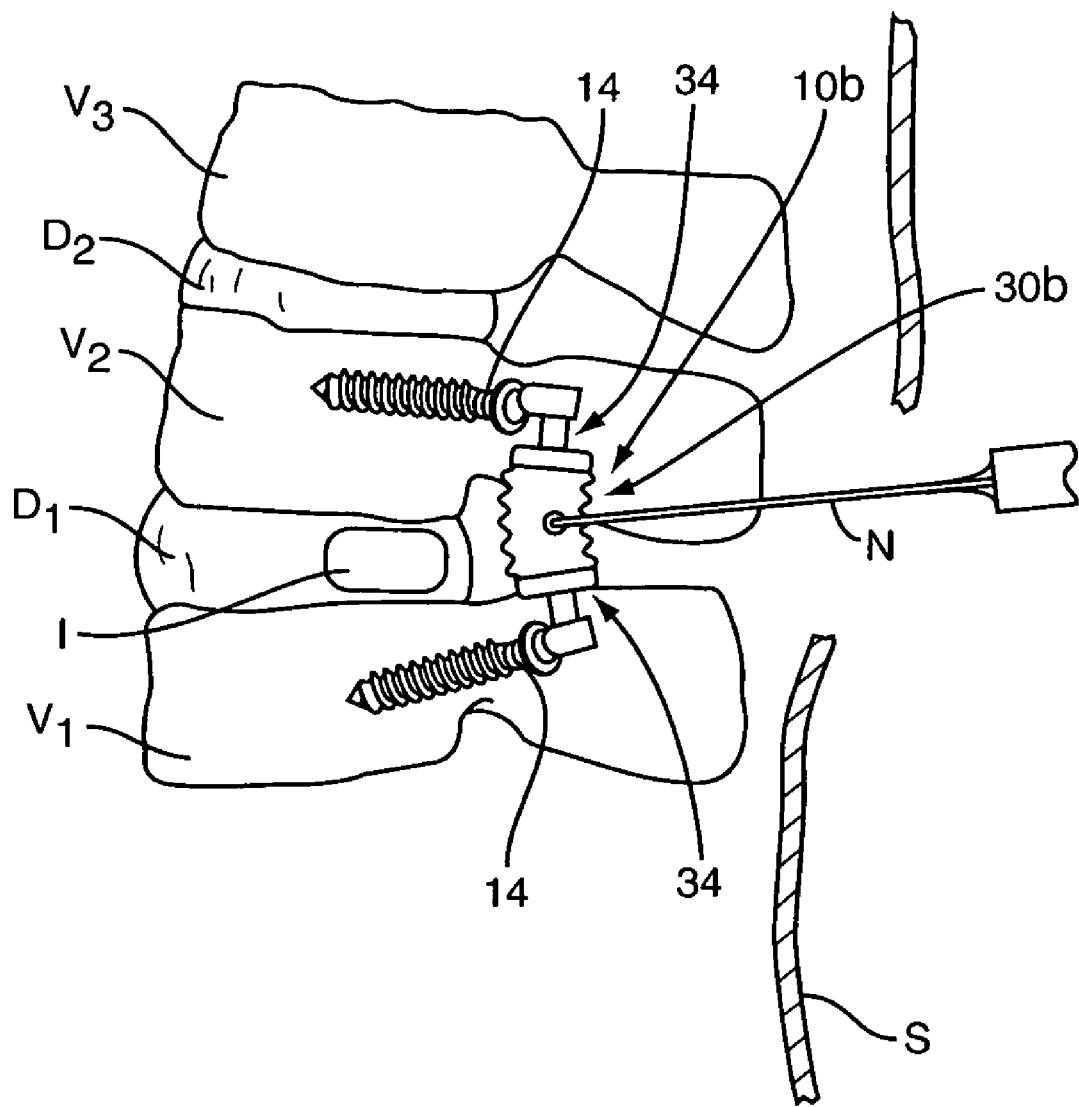
Figure 13:
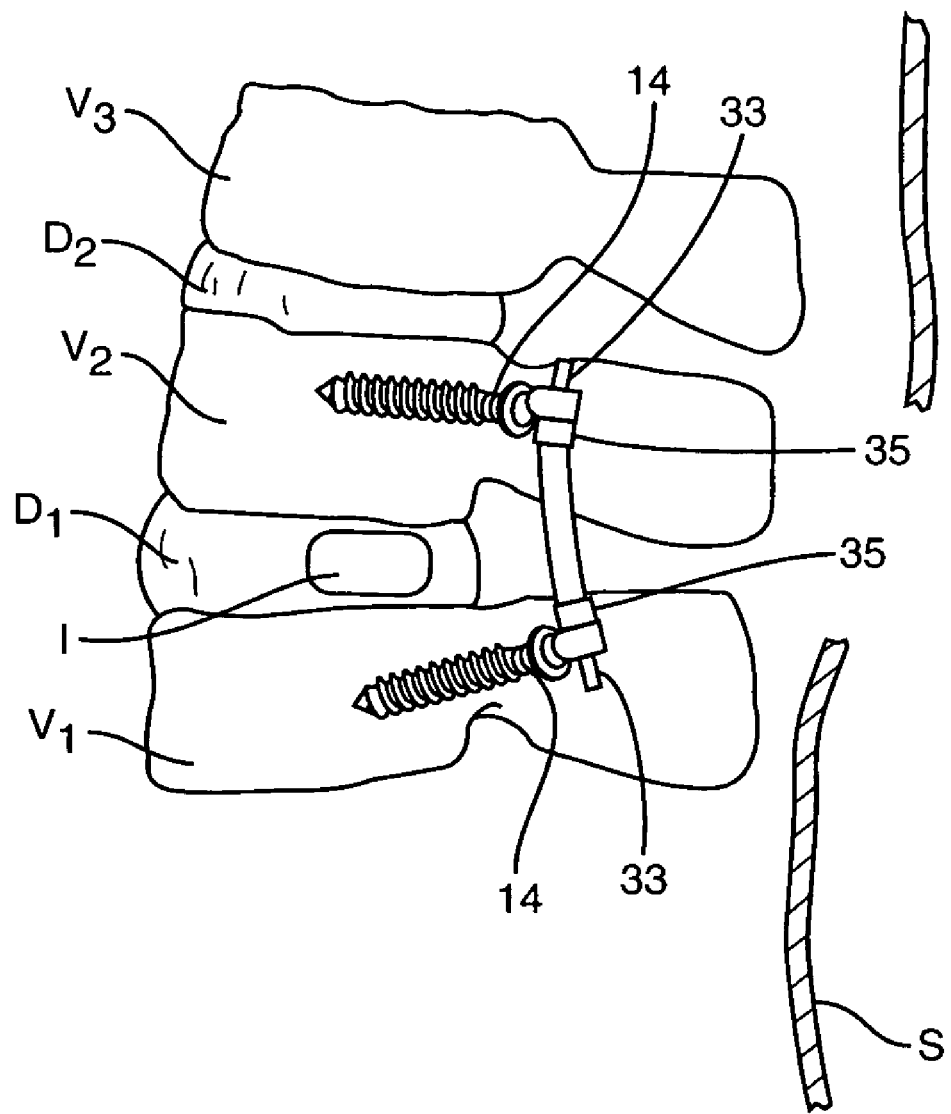

The various rods 10 disclosed herein may be surgically implanted using a variety of techniques. Certainly, full-open surgical procedures that are used to install conventional rods may be used. However, the compressibility of the expandable portion 30 of the rods 10 described herein permits more minimally invasive surgical procedures. FIG. 11 illustrates one such procedure where a mini-open procedure (i.e., with a small surgical incision) is used. FIG. 11 shows a segment of a spine that includes three vertebrae V1, V2, V3 and two discs D1, D2. In this embodiment, the surgical procedure may be necessary to repair a diseased or defective disc D1. Accordingly, a vertebral implant I may be inserted between vertebrae V1 and V2. Pedicle screws 14 similar to those shown in FIG. 1 are inserted into vertebrae V1 and V2 in preparation for the installation of a rod 10. Specifically, FIG. 11 shows rod 10b from FIG. 4 in a compressed and folded condition to pass through a small opening in the subject S. Rod 10b is shown in FIGS. 11-13 for illustrative purposes. In other embodiments, one or more of the other rod 10 embodiments may be inserted using this surgical technique. The opening in the subject S may be widened as needed to allow the rod 10b to pass. The widening may be accomplished using retractors R. Alternatively, the opening may be maintained between screw extenders that are coupled to the installed pedicle screws 14. A dashed-line representation of a portion of exemplary screw extenders is shown in FIG. 11 and identified by the label SE.

The rod 10b is placed into the subject S using an insertion tool, a representation of which is shown in dashed lines and labeled T. Then, the rod 10b is positioned onto the pedicle screws 14 as shown in FIG. 12. At this point, the rod 10b, and particularly the expandable portion 30b remain in a compressed state. Once the rod 10b is positioned as shown, a needle N or other injection instrument is used to inject the injectable substance into the self-sealing valve 58 on the expandable portion 30b. Note that with other embodiments, the injectable substance may be injected into other portions of the rod 10 such as radially or axially into the rod end 34.

As the injectable substance is placed into the expandable portion 30b, the rod ends 32, 34 separate from each other until the enlarged flanges 35 at each rod end 32, 34 contact the head of the pedicle screws 14. The expanded rod 10b is illustrated in FIG. 13. At this point, the rod 10b is fully seated and a suitable clamping device (e.g., retaining cap 16 shown in FIG. 1) can be used to secure the clamping portion 33 to the pedicle screws 14. In an alternative approach, the clamping portions 33 may be secured to the pedicle screws 14 prior to the insertion of some or all of the substance. For example, inserting additional substance into the rod 10b after the clamping portions 33 are secured to the pedicle screws 14 may provide some desired distraction of the vertebrae to which the pedicle screws 14 are attached.

Figure 14:
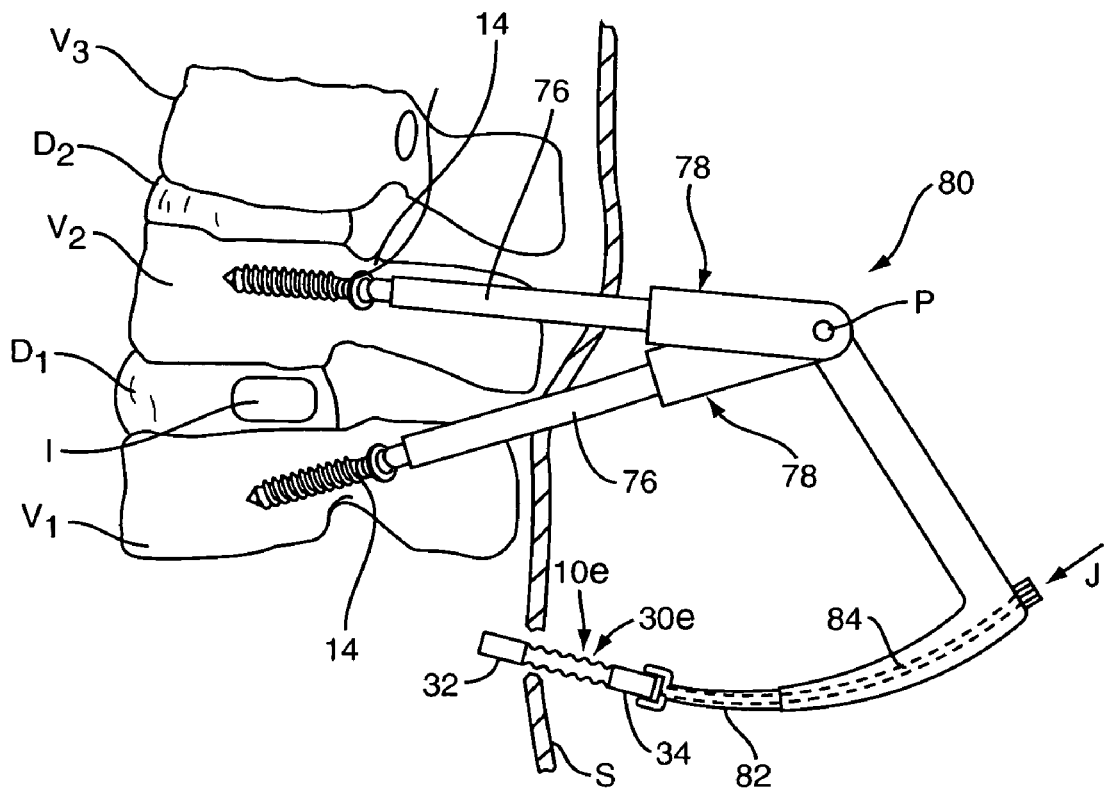
FIGS. 14-15 illustrate a surgical implantation process for a rod according to one embodiment.
Figure 15:
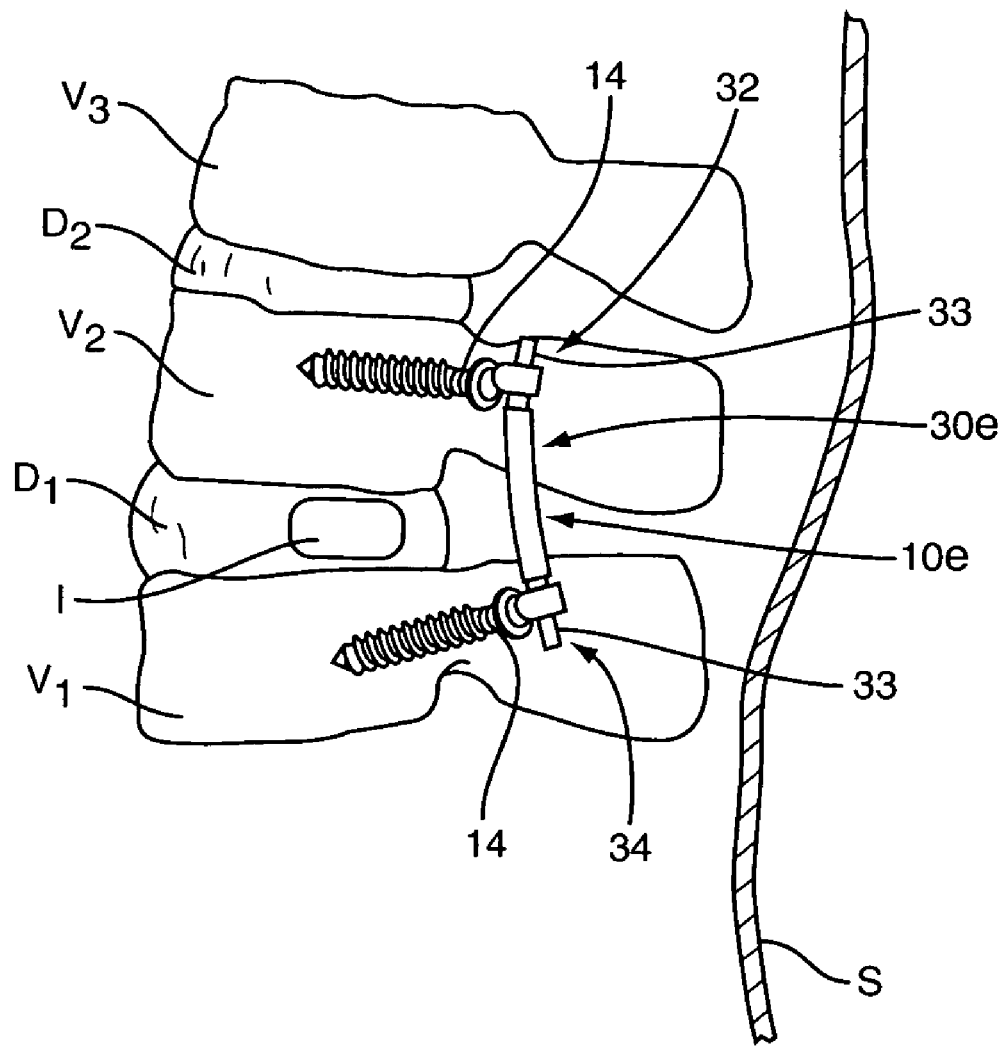

An alternative installation approach contemplates a minimally invasive percutaneous procedure as shown in FIGS. 14 and 15. The procedure shown in FIG. 14 incorporates an installation instrument 80. One example of an instrument suitable for this type of installation is the Sextant Rod Insertion System available from Medtronic Sofamor Danek in Memphis, Tenn., USA. The installation instrument includes support arms 78 that are coupled to pedicle screw extensions 76. The support arms 78 are pivotally connected to a rod holder 82 about pivot P. As with the previous method shown in FIGS. 11-13, this procedure may include removing some or all of an intervertebral disc D1 from the space between first V1 and second V2 vertebral bodies through one percutaneous puncture in the subject. An implant I is introduced into the disc space. Implant I may be an interbody fusion device or the like as is known in the art. The first and second pedicle screws 14 and pedicle screw extensions 76 are engaged to the first and second vertebrae V1, V2, respectively, through second and third percutaneous punctures in the subject S. If desired, a surgeon can manipulate the pedicle screw extensions 76 to apply a load to compress or distract the vertebrae V1, V2 prior to installing rod 10e. Rod 10e is shown for illustrative purposes. Any of the other rod 10 embodiments may be inserted using this technique. The rod 10e is installed through a fourth percutaneous puncture in the subject S using the installation instrument 80. The rod 10e is brought into engagement with the pedicle screws 14 by rotating the rod holder 82 about pivot P.

In one embodiment, the rod holder 82 is cannulated to allow a surgeon to introduce an injectable substance through the rod holder 82 and into the rod 10e. A needle or other injection instrument is used to inject the injectable substance into the port J in the rod holder 82. As the injectable substance is inserted into the expandable portion 30e, the rod ends 32, 34 separate from each other until the clamping portions 33 at each rod end 32, 34 lie within the head of the pedicle screws 14. This is illustrated in FIG. 15. At this point, the rod 10e is fully seated and a suitable clamping device (e.g., retaining cap 16 shown in FIG. 1) can be used to secure the clamping portion 33 to the pedicle screws 14.

Since the rod 10 includes clamping surfaces 33 on either side of an expandable portion 30, a surgeon may clamp down on the rod ends 32, 34 regardless of the phase of the injectable material. That is, regardless of whether the injectable substance is gaseous, liquid, or an uncured liquid, the surgeon may secure the rod 10 to the pedicle screws 14 or other clamping mechanism once the rod ends 32, 34 have expanded to the desired position. This aspect also means a surgeon may be able to secure the rod ends 32, 34 without having to wait for a curable injectable substance to set.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For example, embodiments described above have contemplated end members 32, 34 that have a substantially similar overall shape. However, this is not explicitly required. For instance, other embodiments may include an end member at one end or an intermediate location having a flange while end members in other locations do not have a flange. The present embodiments are, therefore, to be considered in all respects as illustrative and not restrictive, and all changes coming within the meaning and equivalency range of the appended claims are intended to be embraced therein.

What is claimed is:

1. A method of supporting vertebral members, the method comprising the steps of:
    positioning a rod in proximity to the vertebral members while the rod is in a first orientation, the rod including first and second coupling members positioned at opposing ends of an expandable intermediate portion;
    introducing a substance into an interior of the intermediate portion of the rod;
    increasing a length of the rod by axially expanding the intermediate portion and separating the first and second coupling members with the expansion causing the first and second coupling members to seat into anchors mounted to the vertebral members;
    applying a distraction force to the vertebral members by inserting an additional amount of the substance into the interior of the intermediate portion of the rod when the coupling members are seated into the anchors and prevented from moving beyond the anchors;
    after increasing the length of the rod, securing the first and second coupling members to the anchors mounted to the vertebral members.

2. The method of claim 1 wherein increasing the length of the rod and separating the first and second coupling members comprises unfolding a wall.

3. The method of claim 1 wherein increasing the length of the rod and separating the first and second coupling members comprises extending concentric columns.

4. The method of claim 1 further comprising causing the substance to cure after the substance is introduced into the interior of the rod.

5. The method of claim 4 further comprising securing the first and second coupling member prior to causing the substance to cure.

6. A method of supporting vertebral members, the method comprising the steps of:
    filling an interior region of a spinal rod with a substance and increasing an axial length of the spinal rod by expanding the interior region between first and second members and exerting an expansion force to separate the first and second members to a spaced apart configuration;
    separating the first and second members and seating the first and second members in anchors mounted to the vertebral members with a flange on the first member contacting against a first one of the anchors and a flange on the second member contacting against a second one of the anchors, the flanges being wider than portions of the first and second members seated in the anchors;
    applying a distraction force to the vertebral members by filling the interior region with more of the substance; and
    securing the first and second members to the anchors mounted to the vertebral members while the first and second members are in the spaced apart configuration.

7. The method of claim 6 wherein inserting the substance into the interior region of the spinal rod comprises inserting the substance through one of the first and second members.

8. The method of claim 6 further comprising causing the substance to cure after the substance is introduced into the interior region.

9. The method of claim 8 further comprising securing the first and second members to the anchors mounted to the vertebral members prior to causing the substance to cure.

* * * * *